US006849232B2

(12) United States Patent
Ashby et al.

(10) Patent No.: US 6,849,232 B2
(45) Date of Patent: Feb. 1, 2005

(54) METHODS FOR STERILIZING CROSS-LINKED GELATIN COMPOSITIONS

(75) Inventors: Mark Ashby, Laguna Niguel, CA (US); Eduardo C. Sing, Dana Point, CA (US); Richard J. Greff, St. Pete Beach, FL (US)

(73) Assignee: Sub-Q, Inc., San Clemente, CA (US)

( * ) Notice: Subject to any disclaimer, the term of this patent is extended or adjusted under 35 U.S.C. 154(b) by 147 days.

(21) Appl. No.: 10/094,633

(22) Filed: Mar. 12, 2002

(65) Prior Publication Data

US 2002/0190226 A1 Dec. 19, 2002

Related U.S. Application Data

(60) Provisional application No. 60/275,391, filed on Mar. 12, 2001.

(51) Int. Cl.⁷ ............................ A61L 2/08; B65B 55/08; B65B 55/16
(52) U.S. Cl. ..................... 422/22; 424/426; 53/425
(58) Field of Search ..................... 422/22; 424/426; 53/425

(56) References Cited

U.S. PATENT DOCUMENTS

| | | | |
|---|---|---|---|
| 581,235 A | 4/1897 | Kenyon | |
| 1,578,517 A | 3/1926 | Hein | |
| 2,086,580 A | 7/1937 | Shirley | |
| 2,370,319 A | 2/1945 | Lippincott | |
| 2,465,357 A | 3/1949 | Correll | |
| 2,492,458 A | 12/1949 | Bering, Jr. | |
| 2,507,244 A | 5/1950 | Correll | |
| 2,558,395 A | 6/1951 | Studer | |
| 2,597,011 A | 5/1952 | MacMasters et al. | |
| 2,680,442 A | 6/1954 | Linzmayer | |
| 2,761,446 A | 9/1956 | Reed | |
| 2,814,294 A | 11/1957 | Figge | |
| 2,824,092 A | 2/1958 | Thompson | |
| 2,874,776 A | 2/1959 | Hooe | |
| 2,899,362 A | 8/1959 | Sieger, Jr. et al. | |
| 3,157,524 A | 11/1964 | Artandi | |
| 3,358,689 A | 12/1967 | Higgins | |
| 3,411,505 A | 11/1968 | Nobis | |
| 3,724,465 A | 4/1973 | Duchane | |
| 3,736,939 A | 6/1973 | Taylor | |
| 4,000,741 A | 1/1977 | Binard et al. | |
| 4,098,728 A | 7/1978 | Rosenblatt | |
| 4,211,323 A | 7/1980 | Olsen | |
| 4,218,155 A | 8/1980 | Weidner | |
| 4,219,026 A | 8/1980 | Layton | |
| 4,224,945 A | 9/1980 | Cohen | |
| 4,238,480 A | 12/1980 | Sawyer | |
| 4,292,972 A | 10/1981 | Pawelchak | |
| 4,323,072 A | 4/1982 | Rosenbluth et al. | |
| 4,340,066 A | 7/1982 | Shah | |
| 4,390,018 A | 6/1983 | Zuloowski | |
| 4,404,970 A | 9/1983 | Sawyer | |
| 4,405,314 A | 9/1983 | Copi | |
| 4,515,637 A | 5/1985 | Cioca | |
| 4,573,573 A | 3/1986 | Favaro | |
| 4,573,576 A | 3/1986 | Krol | |
| 4,587,969 A | 5/1986 | Gillis | |
| 4,588,395 A | 5/1986 | Lemelson | |
| 4,619,261 A | 10/1986 | Guerriero | |
| 4,619,913 A | 10/1986 | Luck et al. | |
| 4,644,649 A | 2/1987 | Seaman et al. | |
| 4,645,488 A | 2/1987 | Matukas | |
| 4,699,616 A | 10/1987 | Norwak | |
| 4,708,718 A | 11/1987 | Daniels | |
| 4,744,364 A | 5/1988 | Kensey | |
| 4,790,819 A | 12/1988 | Li et al. | |
| 4,829,994 A | 5/1989 | Kurth | |
| 4,832,688 A | 5/1989 | Sagae et al. | |
| 4,836,204 A | 6/1989 | Landymore et al. | |
| 4,839,204 A | 6/1989 | Yoshino | |
| 4,850,960 A | 7/1989 | Grayzel | |
| 4,852,568 A | 8/1989 | Kensey | |

(List continued on next page.)

FOREIGN PATENT DOCUMENTS

| | | |
|---|---|---|
| EP | 0032826 | 7/1981 |
| EP | 0476178 | 3/1992 |
| EP | 0482350 | 4/1992 |
| EP | 0557963 | 2/1993 |
| EP | 0637432 B1 | 7/1994 |
| EP | 0637431 | 11/1994 |
| FR | 2641692 | 7/1990 |
| GB | 1509023 | 4/1978 |
| GB | 1569660 | 6/1980 |
| SU | 782814 | 11/1980 |
| SU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 95/32679 | 12/1995 |
| WO | WO 96/08208 | 3/1996 |
| WO | WO 96/24290 | 8/1996 |
| WO | WO 97/07934 | 3/1997 |
| WO | WO 97/09934 | 3/1997 |
| WO | WO 98/06346 | 2/1998 |
| WO | WO 99/66834 | 12/1999 |

OTHER PUBLICATIONS

Allison, D., et al., "Percutaneous liver biopsy and track embolization with steel coils", Radiology, vol. 169, pp. 261–263, (1998).

(List continued on next page.)

*Primary Examiner*—E. Leigh McKane
(74) *Attorney, Agent, or Firm*—Thelen Reid & Priest, LLP

(57) ABSTRACT

Disclosed are methods for sterilizing cross-linked gelatin as well as to sterilized cross-linked gelatin. In particular, the methods of this invention employ E-beam sterilization techniques.

10 Claims, No Drawings

U.S. PATENT DOCUMENTS

| | | |
|---|---|---|
| 4,869,143 A | 9/1989 | Merrick |
| 4,890,612 A | 1/1990 | Kensey |
| 4,900,303 A | 2/1990 | Lemelson |
| 4,929,246 A | 5/1990 | Sinofaky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,049,138 A | 9/1991 | Chevalier et al. |
| 5,053,046 A | 10/1991 | Janese |
| 5,061,274 A | 10/1991 | Kensey |
| 5,080,655 A | 1/1992 | Haaga |
| 5,108,421 A | 4/1992 | Fowler |
| 5,129,889 A | 7/1992 | Hahn |
| 5,163,904 A | 11/1992 | Lampropoulous et al. |
| 5,167,624 A | 12/1992 | Butler et al. |
| 5,192,290 A | 3/1993 | Hilgal |
| 5,192,300 A | 3/1993 | Fowler |
| 5,192,301 A | 3/1993 | Kamiya et al. |
| 5,195,988 A | 3/1993 | Haaga |
| 5,219,899 A | 6/1993 | Panster et al. |
| 5,220,926 A | 6/1993 | Jones |
| 5,221,259 A | 6/1993 | Weldon et al. |
| 5,232,453 A | 8/1993 | Plass et al. |
| 5,242,683 A | 9/1993 | Klaveness |
| 5,254,105 A | 10/1993 | Haaga |
| 5,275,616 A | 1/1994 | Fowler |
| 5,282,827 A | 2/1994 | Kensey et al. |
| 5,310,407 A | 5/1994 | Casale |
| 5,320,639 A | 6/1994 | Rudnick |
| 5,322,515 A | 6/1994 | Karas et al. |
| 5,325,857 A | 7/1994 | Nabai et al. |
| 5,334,216 A | 8/1994 | Vidal et al. |
| 5,342,388 A | 8/1994 | Toller |
| 5,350,399 A | 9/1994 | Erlebacher et al. |
| 5,352,211 A | 10/1994 | Merskelly |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammersiag |
| 5,385,550 A | 1/1995 | Su et al. |
| 5,388,588 A | 2/1995 | Nabai et al. |
| 5,391,183 A | 2/1995 | Janzen et al. |
| 5,399,361 A | 3/1995 | Song et al. |
| 5,417,699 A | 5/1995 | Klein |
| 5,419,765 A | 5/1995 | Weldon et al. |
| 5,431,639 A | 7/1995 | Shaw |
| 5,437,292 A | 8/1995 | Kipshidze |
| 5,437,631 A | 8/1995 | Janzen |
| 5,443,481 A | 8/1995 | Lee |
| 5,447,502 A | 9/1995 | Haaga |
| 5,458,570 A | 10/1995 | May, Jr. |
| 5,462,194 A | 10/1995 | Barawell |
| 5,467,780 A | 11/1995 | Nabai et al. |
| 5,478,352 A | 12/1995 | Fowler |
| 5,479,936 A | 1/1996 | Nabai et al. |
| 5,486,195 A | 1/1996 | Myers |
| 5,490,736 A | 2/1996 | Haber |
| 5,507,279 A | 4/1996 | Fortune |
| 5,522,840 A | 6/1996 | Krajicek |
| 5,522,850 A | 6/1996 | Yomtov et al. |
| 5,526,822 A | 6/1996 | Burbank et al. |
| 5,527,332 A | 6/1996 | Clement |
| 5,529,577 A | 6/1996 | Hammershiag |
| 5,540,715 A | 7/1996 | Katseros et al. |
| 5,542,914 A | 8/1996 | Van Iten |
| 5,545,175 A | 8/1996 | Abidin et al. |
| 5,545,178 A | 8/1996 | Kensey et al. |
| 5,558,853 A | 9/1996 | Quay |
| 5,571,168 A | 11/1996 | Toro |
| 5,591,204 A | 1/1997 | Janzen et al. |
| 5,591,205 A | 1/1997 | Fowler |
| 5,601,601 A | 2/1997 | Tal et al. |
| 5,601,602 A | 2/1997 | Fowler |
| 5,601,603 A | 2/1997 | Illi |
| 5,620,461 A | 4/1997 | Muijs Van De Moer |
| 5,645,566 A | 7/1997 | Brennenman et al. |
| 5,649,547 A | 7/1997 | Ritchart et al. |
| 5,653,730 A | 8/1997 | Hammersiag |
| 5,665,107 A | 9/1997 | Hammersiag |
| 5,674,346 A | 10/1997 | Kundel ................... 156/272.2 |
| 5,676,689 A | 10/1997 | Kensey |
| 5,681,279 A | 10/1997 | Roper et al. |
| 5,707,393 A | 1/1998 | Kensey et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,830,130 A | 11/1998 | Janzen et al. |
| 5,858,008 A | 1/1999 | Capaccio |
| 5,868,762 A | 2/1999 | Cragg et al. |
| 5,902,310 A | 5/1999 | Foerster et al. |
| 5,931,165 A | 8/1999 | Reich et al. ................. 128/898 |
| 5,984,950 A | 11/1999 | Cragg et al. |
| 6,007,563 A | 12/1999 | Nash et al. |
| 6,027,471 A | 2/2000 | Fallon et al. |
| 6,027,482 A | 2/2000 | Imbert |
| 6,033,427 A | 3/2000 | Lee |
| 6,056,768 A | 5/2000 | Cates et al. |
| 6,066,325 A | 5/2000 | Wallace et al. ............. 424/400 |
| 6,071,300 A | 6/2000 | Brenneman et al. |
| 6,071,301 A | 6/2000 | Cragg et al. |
| 6,086,607 A | 7/2000 | Cragg et al. |
| 6,090,130 A | 7/2000 | Nash et al. |
| 6,126,675 A | 10/2000 | Shchervinsky et al. |
| 6,161,034 A | 12/2000 | Burbank et al. |
| 6,162,192 A | 12/2000 | Cragg et al. |
| 6,183,497 B1 | 2/2001 | Sing et al. |
| 6,200,328 B1 | 3/2001 | Cragg et al. |
| 6,315,753 B1 | 11/2001 | Cragg |
| 6,371,974 B1 | 4/2002 | Brenneman et al. |
| 6,440,151 B1 | 8/2002 | Cragg et al. |
| 6,440,153 B2 | 8/2002 | Cragg et al. |
| 6,477,534 B1 | 9/2002 | Cragg et al. |
| 6,503,222 B2 | 1/2003 | Lo |
| 6,527,734 B2 | 3/2003 | Cragg et al. |
| 6,540,735 B1 | 4/2003 | Ashby et al. |
| 6,544,236 B1 | 4/2003 | Cragg et al. |
| 6,610,026 B2 | 8/2003 | Cragg et al. |
| 2002/0002889 A1 | 1/2002 | Ashby et al. |
| 2002/0016612 A1 | 2/2002 | Ashby et al. |
| 2002/0038133 A1 | 3/2002 | Chi Sing et al. |
| 2002/0042378 A1 | 4/2002 | Reich et al. |
| 2002/0062104 A1 | 5/2002 | Ashby et al. |
| 2002/0156495 A1 | 10/2002 | Brenneman et al. |
| 2003/0028140 A1 | 2/2003 | Greff et al. |
| 2003/0088269 A1 | 5/2003 | Ashby |
| 2003/0088271 A1 | 5/2003 | Cragg et al. |
| 2003/0120258 A1 | 6/2003 | Ashby et al. |
| 2003/0135237 A1 | 7/2003 | Cragg et al. |
| 2004/0019328 A1 | 1/2004 | Chi Sing et al. |
| 2004/0019330 A1 | 1/2004 | Ashby |

OTHER PUBLICATIONS

J. Bryne Review Article: Endovascular treatments for intracranial anuerysms, 1996 The British journal of radiology; 98,891–899.

Chuang, V., et al., "Sheath needle for liver biopsy in high–risk patience", Radiology, vol. 166, pp. 261–262 (1988).
John T. Correll, et al., A new Physiologically absorbable sponge, prior art.
John T. Correll, et al. Biologic investigations of new absorbable sponge; p. 585, prior art.
Fandrich, C., et al. "Small guage gelfoam plug liver biopsy in high risk patients", Australian Radiolgy, vol. 40, pp. 230–234 (1996).
Foran, JPM, et al. "Early mobilisation after percutaneous cardiac catheterisation using collagen plug (vasoseal) maemostatis" BRHeart, vol. 69, pp. 424–429 (1993).
Gibbs, JSR, "Femoral arterial hemostasis" J. Interventional card, vol. 5, pp. 85–88 (1992).
Journal of interventional cardiology vol. 5 No. 2, prior art.
Kassell, et al. Size of Intracanial aneurysm; vol. 12, No. 3, (1983).
Kiemeneiji, F, et al., "Improved anticoagulation management after Palmaz Schatz coronary stent implantation by sealing the arterial puncture site with vascular hemostasis device", Catheterization and Cardiovascular diagnosis, vol. 30, pp. 1685–1692 (1995).
Kussmaul, WG, "Rapid arterial hemostasis", J. Am. Coll. Card., vol. 25, pp. 1685–1692 (1995).
Pharmacia & Upjohn manufacturer brochure gelfoam sterile sponge, sterile powder and sterile film, pp 1–34 (May 1997).
Pharmacia & Upjohn manufacturer brochure "gelfoam sterile powder", (Feb. 1996).
Pharmacia & Upjohn manufacturer brochure, "gelfoam sterile powder" (Mar. 1996).
Pharmacia & Upjohn manufacturer brochure (Feb. 1996).
Pharmacia & Upjohn manufacturer specification, "Gelfoam sterile sponge, sterile powder and sterile film" pp. 1–23 (Nov. 1996).
Riley, SA, Percutaneous liver biopsy with plugging of needle track: a safe method for use in patients with impaired coagulation, The lancet, p. 436 (1964).
Sanborn, T. Multicenter randomized trial comparing perutaneous collagen hemostasis device with conventional manual compression after diagnostic angiography and angioplasty , J. Am. Coll. Card., vol. 22, pp. 1273–1279, (1993).
Schievink, et al. The new england journal of medicaine; review articles; intracanial aneurysms; Jan. 2 1997.
Scharader, R. "Collagen appl.", Catheterization & cardiovascular diagnosis (1992) pp. 298–302.
Silber, S., "Rapid hemostasis of arterial puncture sites with collagen in patients undergoing diagnostic interventional cardiac catherterization", clinical cardiology, vol. 20, pp. 981–992, (1997).
Smith, T., "Percutaneous transhepatic liver biopsy with tract embolization", Radiology, vol. 198, pp. 769–774 (1996).
Szikora, et al. Combined Use of stents and cells to treat experimental wide–necked carotid aneuryms: Preliminary results; AJNR AM newradiol 15: 1091–1102, Jun.'94.
Szikora, et al. Endovascular treatment of experimental anuerysms with liquid polymers: vol. 38, No. 2, Feb.'96.
Turjman, et al. Combined stent implantation & endosacular coil placement for tretment of experimental wide–necked aneurysms:AJNRAM J. Neuroradio 15: 1087–1090 Jun.'94.

Yoshimoto, et al cerebral anuerysms unrelated to arterial bifurcations; Acta neurochir (Wien) (96) 138: 958–964.
Zins, M., "US–guided percutaneous liver biopsy with plugging of the needle track" radiology, vol. 187, pp. 841–843, (1992).
Berman, Howard L., et al, "Guided Direct Antegrade Puncture of the Superficial Femoral Artry," American Roantgen Ray Society, pp. 632–634 (Sep. 1986).
Berman et al "Modification of the Cope Drainage Catheter to Facilitate Placement" AJR 146:169–170, Jan. 1986 0361–803X/86/1461–0169 © American Ray Society.
Saddekni, Sovhell, M.D., et al "Antegrade Cathererization of the Superficial Femoral Artery," Radiology, 157:531–532 (1985).
Vogelzang, Robert L., "A Modified Cope Introducing Dilator to Allow Straight Guide Wire Introduction," American Roantigen Ray Society, pp. 381–382 (Feb. 1986).
(125) Ashby, Mark et al; U.S. Appl. No. 10/287,922; filed: Nov. 4, 2002; entitled: Apparatus And Method For Inhibiting Blood Loss.
(130) Ashby, Mark et al; U.S. Appl. No. 10/069,107; filed: Dec. 16, 2002; entitled: Device And Method For Determining A Depth Of An Incision.
(144) Ashby, Mark et al; U.S. Appl. No. 10/278,710; filed Oct. 22, 2002; entitled: System and Method for Facilitating Hemostasis of Blood Vessel Punctures With Absorbable Sponge.
(152) Ashby, Mark et al; U.S. Appl. No. 10/334,770; filed: Dec. 31, 2002; entitled: Improved System and Method for Facilitating Hemostasis with Absorbable Sponge.
(154) Ashby, Mark et al; U.S. Appl. No. 10/421,680; filed Apr. 22, 2003; entitled: Puncture Closure System With Pin And Pull Technique.
(159) Ashby, Mark et al; U.S. Appl. No. 10/462,065; filed: Jun. 12, 2003; entitled: Enhanced Bleed Back System.
(160) Ashby, Mark et al, U.S. Appl. No. 10/462,064; filed: Jun. 12, 2003; entitled: Release Mechanism.
(161) Ashby, Mark et al; U.S. Appl. No. 10/461,587; filed: Jun. 12, 2003; entitled: Dissolvable Closure Device.
(162) Ashby, Mark et al; U.S. Appl. No. 10/461,035; filed: Jun. 13, 2003; entitled: System And Method For Delivering Hemostasis Promoting Material To A Blood Vessel Puncture Site Using a Cannula.
(163) Ashby, Mark et al; U.S. Appl. No. 10/461,006; filed: Jun. 13, 2003; entitled: System and Method for Delivering Hemostasis Promoting Material to a Blood Vessel Puncture with a Staging Tube.
(164) Ashby, Mark et al; U.S. Appl. No. 10/460,859; filed: Jun. 12, 2003; entitled: Hemostatic Device Including a Capsule.
(187) Ashby, Mark et al; U.S. Appl. No. 10/732,441; filed: Dec. 9, 2003; entitled: Pledget–Handling System and Method for Delivering Hemostasis Promoting Material to a Blood Vessel Puncture Site By Fluid Pressure.
(190) Ashby, Mark et al; U.S. Appl. No. 10/754,824; filed: Jan. 9, 2004; entitled: Sheath–Mounted Arterial Plug Delivery Device.

METHODS FOR STERILIZING CROSS-LINKED GELATIN COMPOSITIONS

This application claims priority under 35 U.S.C. §119 to U.S. Provisional Application No. 60/275,391 entitled Methods for Sterilizing Cross-Linked Gelatin Compositions and filed on Mar. 12, 2001, the entire content of which is hereby incorporated by reference.

BACKGROUND OF THE INVENTION

1. Field of the Invention

This invention is directed to methods for sterilizing cross-linked gelatin as well as to sterilized cross-linked gelatin compositions possessing novel properties. In particular, the methods of this invention employ E-beam irradiation to sterilize cross-linked gelatin.

2. References

The following patent applications and patents are cited and/or reference in this application as superscript numbers:

[1] Correll, et al., Proc. Soc. Exp. Biol. N.Y., 58:233 (1945)

[2] Correll, et al., Surg. Gyn. and Obst., 82:585 (1945)

[3] Correll, et al., U.S. Pat. No. 2,465,357, Therapeutic Sponge and Method of Making, issued Mar. 29, 1949

[4] Correll, et al., U.S. Pat. No. 2,507,244, Surgical Gelatin Dusting Powder and Process for Preparing Same, issued May 9, 1950

[5] Studer, et al., U.S. Pat. No. 2,558,395, Undenatured Gelatin Hemostatic Sponge Containing Thrombin, issued Jun. 26, 1951

[6] Sieger, et al., U.S. Pat. No. 2,899,362, Hemostatic Sponges and Method of Preparing Same, issued Aug. 11, 1959

[7] Song, et al., U.S. Pat. No. 5,399,361, Collagen-containing Sponges as Drug Delivery Compositions for Proteins, issued Mar. 21 1995

[8] Cragg, et al., U.S. Pat. No. 6,071,301, Device and Method for Facilitating Hemostasis of a Biopsy Tract, issued Jun. 6, 2000

[9] Cragg, et al., U.S. Pat. No. 6,086,607, Device and Method for Facilitating Hemostasis of a Biopsy Tract, issued Jul. 11, 2000

[10] Cragg, et al., U.S. Pat. No. 6,162,192, System and Method for Facilitating Hemostasis of Blood Vessel Punctures with Absorbable Sponge, issued Dec. 19, 2000

[11] Pawelchak, et al., U.S. Pat. No. 4,292,972, Lyophilized Hydrocolloid Foam, issued Oct. 6, 1981

[12] Sawyer, U.S. Pat. No. 4,238,480, Method for Preparing an Improved Hemostatic Agent and Method of Employing the Same, issued Dec. 9, 1980

[13] Sawyer, U.S. Pat. No. 4,404,970, Hemostatic Article and Method for Preparing and Employing the Same, issued Sep. 20, 1983

All of the above patent applications and patents are herein incorporated by reference in their entirety to the same extent as if each individual publication, patent application or patent was specifically and individually indicated to be incorporated by reference in its entirety.

3. State of the Art

Cross-linked gelatin, often in the form of gelatin foam, gelatin film or gelatin sponges, has been used as a hemostatic agent since its development by Correll in 1945.[1-4] In addition, medicaments, such as antibiotics, growth factors and thrombus enhancing agents, have been incorporated into the cross-linked gelatin to enhance the in vivo properties of the composition.[5-7]

When used as a hemostatic agent, the cross-linked gelatin is placed on or in the body and, accordingly, the composition must be sterilized before use, Conventionally, sterilization of these cross-linked gelatin compositions is conducted at elevated temperatures for prolonged periods of time, e.g., 130° to 140° C. for 3 hours as described by Correll.[3] While the resulting cross-linked gelatin composition is sterile, the sterilization process causes chemical reactions within the cross-linked gelatin (polypeptide) which results in hardening and insolubilization of the gelatin. These changes can be correlated with the tensile strength and fluid (e.g., water, blood, etc.) uptake of the cross-linked gelatin composition before and after heat sterilization and the heat sterilized product has higher tensile strength and significantly less fluid uptake as compared to the pre-sterilized product.

One particular use of cross-linked gelatin described in the art is to facilitate hemostasis of a puncture site such as a puncture wound resulting from catheter insertion or a biopsy needle. When so used, the art describes ejection of a pledget of cross-linked gelatin from a syringe into the puncture site.[8-10]

Critical to the ejection process is the flowability of the pledget from the syringe assembly and retention of its structural integrity during insertion into the body. Specifically, ejection of the pledget from the syringe assembly is preferably conducted with, at most, moderate pressure to ensure accurate placement in vivo which relates to the flowability of the cross-linked gelatin. Higher fluid content pledgets are believed to correlate with enhance flowability and, accordingly, it is desirable to maintain as high a fluid absorbability content in the sterilized pledget as possible.

Likewise, it is critical that the structural integrity of the pledget is substantially maintained as it is ejected from the syringe assembly when placed in vivo in order to ensure that portions of the pledget are not torn or otherwise separated from the pledget. This criticality is particularly important when placed over a blood vessel puncture in order to avoid unintended thrombosis of the vessel. Structural integrity of the gelatin composition of the pledget under pressure is believed to correlate with the tensile strength of the composition and, accordingly, it is desirable to maintain as high a tensile strength in the sterilized pledget as possible.

However, as demonstrated in the Examples below, the heat sterilization processes of the prior art significantly reduce the water absorbability of the cross-linked gelatin and only modestly increase its tensile strength. In addition, heat sterilized gelatin has a significant drawback when packaged within a device for use because dry heat sterilization requires prolonged heating at elevated temperatures (e.g., 140° C. for 8 hours for a metal component to be sterilized). Notwithstanding such prolonged heating, these processes are often ineffective in reducing bioburden to a level recognized to effect sterility. The possibility of ethylene oxide or gamma ($\gamma$) sterilization of gelatin has also been mentioned in the literature.[11-13] However, these methods cause irreversible reactions within the gelatin leading to altered and possibly undersirable physical and biological properties.

As is apparent, methods for sterilizing cross-linked gelatin compositions without significant reductions in fluid absorbability while significantly increasing its tensile strength would be of great value. In addition, it would be particularly valuable if such methods would sterilize packaged gelatin compositions, such as those contained within finished medical devices such as a delivery system of syringes, syringes, or other assemblies in order to facilitate manufacture of sterile devices.

SUMMARY OF THE INVENTION

This invention is directed to methods for sterilizing cross-linked gelatin compositions. In particular, this invention is directed to the novel and unexpected result that, under carefully controlled conditions, cross-linked gelatin compositions, including packaged gelatin compositions, can be sterilized using E-beam irradiation at room temperature conditions. This invention is further directed to the discovery that the E-beam cross-linked sterilized gelatin compositions retain a significantly greater amount of fluid absorbability and tensile strength as compared to heat sterilized cross-linked gelatin compositions.

In a further aspect, it has been discovered that packaged cross-linked gelatin composition can be sterilized by employing a sufficiently energetic E-beam source coupled with an average bulk density of the materials comprising the packaging elements of no more than about 0.2 g/cm$^3$. When so employed, the E-beam sterilizes the package and the cross-linked gelatin composition therein.

In both embodiments, preferred E-beam dosages are from of about 5 to 50 kGray and preferably from about 15 to 25 kGray.

Accordingly, in one of its method aspects, this invention is directed to a method for sterilizing a cross-linked gelatin composition which method comprises exposing the cross-linked gelatin composition to a sufficient dose of E-beam irradiation under conditions wherein said composition is sterilized.

In another of its method aspects, this invention is directed to a method for preparing a sterile, cross-linked gelatin composition in a packaging element wherein the method comprises:

(a) selecting a packaging element;

(b) adding said cross-linked gelatin composition to the packaging element selected in (a) above; and (c) exposing the packaging element formed in (b) above to a sufficient dosage of E-beam irradiation maintained at an initial fluence of at least 5 μCurie/cm$^2$ to sterilize both the packaging element and the cross-linked gelatin composition therein wherein the average bulk density of the materials comprising the packaging element is less than about 0.2 gm/cm$^3$.

As noted above, the E-beam sterilized cross-linked gelatin compositions retain a significantly greater amount of fluid absorbability and tensile strength as compared to heat sterilized cross-linked gelatin compositions. Accordingly, in one of its composition aspects, this invention is directed to a sterilized cross-linked gelatin composition characterized by a fluid absorbability of at least 30 grams of fluid per gram of gelatin and a tensile strength of greater than 2.0 lbs/in$^2$.

In a preferred embodiment, the sterilized cross-linked gelatin composition has a fluid absorbability of at least 35 grams of fluid per gram of gelatin and a tensile strength of greater than 2.5 lbs/in$^2$.

In another preferred embodiment, the sterilized cross-linked gelatin composition comprises a medicament such as an antimicrobial agent (e.g., an antibiotic), growth factors, thrombus enhancing agents, and the like or a property modifying agent such as a wetting agent. Mixtures of medicaments and property modifying agents can also be used. Suitable medicaments can be mixed with or impregnated into the cross-linked gelatin composition prior to E-beam sterilization. Incorporation of biocompatible wetting agents into a cross-linked gelatin composition is typically conducted prior to E-beam sterilization. Incorporation of such wetting agents is described in U.S. Provisional Patent Application Serial No. 60/275,420 entitled "Cross-Linked Gel Compositions Comprising a Wetting Agent", and U.S. patent application Ser. No. 10/068,812, also entitled "Cross-Linked Gel Compositions Comprising a Wetting Agent", which applications are incorporated herein by reference in their entirety.

In still another of its method aspects, this invention is directed to a method for preparing a sterile syringe assembly comprising a cross-linked gelatin composition wherein said syringe assembly is included in a packaging element which method comprises:

(a) selecting a syringe assembly comprising a holding chamber an injection port which comprising a luer hub and an ejection port which is attached to a cannula;

(b) adding to the holding chamber of said syringe assembly a cross-linked gelatin composition in the form of a pledget;

(c) adding sterile saline to said holding chamber wherein sufficient amounts of said saline are added to hydrate said pledget;

(d) transferring the hydrated pledget into the cannula attached to the ejection port;

(e) combining at least a single syringe produced in (d) above into a packaging element;

(f) exposing the packaging element formed in (e) above to a sufficient dosage of E-beam irradiation maintained at an initial fluence of at least 5 μCurie/cm$^2$ to sterilize the packaging element and the syringe and the gelatin composition therein wherein the average bulk density of the materials comprising the packaging element is less than about 0.2 gm/cm$^3$.

Preferably, the packaging element is a poly-Tyvec packaging such as that which available from Mangar Corp., City of Industry, Calif., USA.

Preferably, the initial fluence of E-beam radiation is preferably at 10 μCurie/cm$^2$ and, more preferably, at least 5 μCurie/cm$^2$.

More preferably, each packaging element comprises from 1 to about 20 syringes and even more preferably from 1 to 2 syringes.

DETAILED DESCRIPTION OF THE PREFERRED EMBODIMENTS

This invention is directed to methods for sterilizing cross-linked gelatin as well as to sterilized cross-linked gelatin. Prior to describing this invention in further detail, the following terms will first be defined.

Definitions

As used herein, the following terms have the following meanings:

The term "cross-linked gelatin" refers to well known gelatin foams, films or sponges which are cross-linked with a conventional cross-linking agent such as formaldehyde as described in the art by Correll.[1-3] The term "cross-linked gelatin composition" refers to compositions comprising cross-linked gelatin. Such compositions often include other components such as a medicament[8-10] or a second polymer such as collagen[13] or starch.[6]

The term "growth factors" refer to those medicaments which are conventionally employed to facilitate tissue growth such as the endothelial wall of a punctured blood vessel. Examples of suitable growth factors include PDGF, EGF, FGF, IGF, TGF, and the like.

The term "thrombus enhancing agents" refer to those medicaments which are conventionally employed to facilitate thrombus formation at a puncture site such as at the endothelial wall of a punctured blood vessel. Examples of suitable thrombus enhancing agents include thrombin, fibrinogen, factor XIII, and other coagulation factors.

The term "antimicrobial agent" refers to agents which destroy microbes (i.e., bacteria, fungi, viruses and microbial spores) thereby preventing their development and pathogenic action. Preferred antimicrobial agents include antibiotics and antiviral agents and, in particular, antibiotics.

The term "initial fluence" of E-beam radiation refers to the fluence of this beam immediately after release from the E-beam accelerator. As is well known, the fluence of an E-beam will be reduced the further it travels from the source.

The term "packaging element" refers to those packaging components used to encase the cross-linked gelatin and include, by way of example, boxes, syringes, envelops, tubings, catheters, introducers and the like. The packaging elements may comprise glass, plastic, paper, ceramics, cardboard, and the like.

The term "average bulk density" refers to the weight of total product to be sterilized divided by its volume.

The term "syringe assembly" refers to the syringe body comprising an open proximal end which acts as the addition port of said syringe, an open distal end which acts as the ejection port of said syringe, a cavity between said proximal and distal ends which acts as a holding chamber for said syringe, and a plunger which, when activated, acts to eject material residing in the holding chamber out of the distal end of the syringe assembly.

Methods

The methods of this invention involve E-beam sterilization of a cross-linked gelatin composition which method comprises exposing the cross-linked gelatin composition to a sufficient dose of E-beam irradiation under conditions wherein said composition is sterilized.

In a preferred embodiment, the cross-linked gelatin composition to be sterilized comprises a medicament such as an antimicrobial agent (e.g., an antibiotic), growth factors, thrombus enhancing agents, and the like or a property modifying agent such as a wetting agent. Mixtures of medicaments and property modifying agents can also be used. Suitable medicaments can be mixed with or impregnated into the cross-linked gelatin composition prior to E-beam sterilization. Incorporation of biocompatible wetting agents into a cross-linked gelatin composition is typically conducted prior to E-beam sterilization. Incorporation of such wetting agents is described in U.S. Provisional Patent Application Serial No. 60/275,420 entitled "Cross-Linked Gel Compositions Comprising a Wetting Agent", and U.S. patent application Ser. No. 10/068,812, also entitle "Cross-Linked Gel Compositions Comprising a Wetting Agent", which applications are incorporated herein by reference in their entirety.

When employed, the medicament is utilized in an amount sufficient for its intended purpose, e.g., an antimicrobially effective amount, an amount sufficient to induce thrombus formation, an amount sufficient to promote growth. The specific amount employed relates to the effectiveness of the medicament, the disease condition of the patient being treated, the age and weight of the patient, the location of the disease and other factors well within the purview of the attending clinician.

Also when employed, the wetting agent is utilized in an amount sufficient to decrease the time to fully hydrate the composition. Preferably, the cross-linked gelatin composition will comprise from about 0.001 to about 20 weight percent of the wetting agent based on the total weight of the composition. Preferably, the composition comprises from about 0.005 to about 10 weight percent.

The dose of E-beam radiation employed is one sufficient to sterilize the cross-linked gelatin composition. In a preferred embodiment, the E-beam dosage is preferably from about 5 to 50 kGray and more preferably from about 15 to about 25 kGray with the specific dosage being selected relative to the quantity of cross-linked gelatin composition to be sterilized as well as the amount of bioburden estimated to be thereon. Such factors are well within the skill of the art. Upon completion of the sterilization process, the sterilized product is ready for shipment to the ultimate user.

E-beam sterilization is preferably conducted at ambient atmospheric conditions such as a temperature of from about 15° C. to about 30° C. and the exposure time of the product to the E-beam radiation is dependent on the fluence of the radiation employed and the dosage required which is well within the skill of the art. Preferably, exposure time of the product to the E-beam is less than 5 minutes and, more preferably, from about 1 to about 180 seconds.

Preferably, the composition is exposed to E-beam irradiation having an initial fluence of at least 5 $\mu$Curie/cm$^2$ and, more preferably, from at least 5 $\mu$Curie/cm$^2$ to at least 15 $\mu$Curie/cm$^2$ and an E-beam dosage are from of about 5 to 50 kGray and more preferably from about 15 to 25 kGray.

The E-beam sterilized cross-linked gelatin compositions retain a significantly greater amount of fluid absorbability and tensile strength as compared to heat sterilized cross-linked gelatin compositions. For example, the E-beam sterilized cross-linked gelatin composition described herein preferably have a fluid absorbability of at least 30 grams of fluid per gram of gelatin and a tensile strength of greater than 2.0 lbs/in$^2$.

In a more preferred embodiment, the sterilized cross-linked gelatin composition has a fluid absorbability of at least 35 grams of fluid per gram of gelatin and a tensile strength of greater than 2.5 lbs/in$^2$.

In another embodiment, the E-beam sterilization methods of this invention can be used to sterilize a packaging element comprising a cross-linked gelatin composition. When so employed, it is necessary to ensure that the packaging element comprising the cross-linked gelatin composition is exposed to a sufficient dosage of E-beam irradiation maintained at an initial fluence of at least 5 $\mu$Curie/cm$^2$ to sterilize the packaging element and its contents. Because of the low penetrating capacity of the E-beams, the average bulk density of the materials comprising the packaging element should be less than about 0.2 gm/cm$^3$.

In one embodiment, the packaging element comprises the syringe and, in another, the syringe is further packaged into a box or other suitable container. In the latter embodiment, the average bulk density of the packaging element is measured relative to the syringe and the container and the container contain from 1 to about 20 syringes but preferably from 1 to 2 syringes.

Utility

The methods of this invention are useful in providing sterilized cross-linked gelatin compositions which can then be used as hemostatic agents for use with mammals and, in particular, humans.

The following example illustrates certain embodiments of the invention but are not meant to limit the scope of the claims in any way.

EXAMPLE

In the example below, all temperatures are in degrees celsius (unless otherwise indicated) and all percents are weight percent (also unless otherwise indicated). Additionally, the following abbreviations have the following meanings. If an abbreviation is not defined, it has its generally accepted meaning.

| | | |
|---|---|---|
| $cm^2$ | = | square centimeter |
| g | = | gram |
| kGy or kGray | = | kiloGray |
| lbs | = | pounds |
| μCuries | = | microcurie |
| USP | = | US Pharmacopia |

Example

Sterilization of Cross-Linked Gelatin Compositions

Three gelatin compositions were cross-linked with approximately 0.01 equivalents of formaldehyde. The first sample (Sample A) was used as unsterilized control, the second sample (Sample B) was E-beam sterilized by E-beams for a period of about 30 seconds to provide for a dose of about 17–25 kGy; and the third sample (Sample C) was heat sterilized by exposure of the sample to a temperature of approximately 130° C. for about 3 hours.

The color, tensile strength and fluid uptake properties of each of the samples was then determined and are repeated below:

| | Color | Tensile Strength | Water Uptake |
|---|---|---|---|
| Sample A | White | 1.5 lbs/in$^2$ | 42 g/g |
| Sample B | White | 2.7 lbs/in$^2$ | 36 g/g |
| Sample C | Off White | 2.0 lbs/in$^2$ | 28 g/g |

The color was determined visually. Water uptake was measured per the USP test for absorbable gelatin. Tensile strength was determined conventionally using a Chatillion gauge.

The above example demonstrates that E-beam irradiation of cross-linked gelatin provides for sterilized compositions having significantly higher tensile strength and water uptake properties as compared to heat sterilized cross-linked gelatin.

From the foregoing description, various modifications and changes in the composition and method will occur to those skilled in the art. All such modifications coming within the scope of the appended claims are intended to be included therein.

What is claimed is:

1. A method for sterilizing a cross-linked gelatin composition for use in vivo, comprising:
    exposing the cross-linked gelatin composition to a sufficient dose of E-beam irradiation under conditions wherein said composition is sterilized and wherein said cross-linked gelatin composition retains a sufficient amount of fluid absorbability of about 35 grams of fluid per gram of gelatin.

2. The method of claim 1 wherein the cross-linked gelatin composition retains a sufficient amount of tensile strength.

3. A method for sterilizing a cross-linked gelatin composition for use in vivo, comprising:
    exposing the cross-linked gelatin composition to a sufficient dose of E-beam irradiation under conditions wherein said composition is sterilized and wherein said cross-linked gelatin composition retains a tensile strength of about 2.5 lbs/in2.

4. The method of claim 3 wherein the cross-linked gelatin composition retains a sufficient amount of fluid absorbability.

5. A method for preparing a sterile, cross-linked gelatin composition in a packaging element, said cross-linked gelatin for use in vivo, the method comprising:
    (a) selecting a packaging element;
    (b) adding said cross-linked gelatin composition to the packaging element selected in (a) above; and
    (c) exposing the packaging element formed in (b) above to a sufficient dosage of E-beam irradiation maintained at an initial fluence of at least 5 μCurie/cm$^2$ to sterilize both the packaging element and the cross-linked gelatin composition therein wherein the average bulk density of the materials comprising the packaging element is less than about 0.2 gm/cm$^3$ and wherein said cross-linked gelatin composition retains a sufficient amount of fluid absorbability and tensile strength.

6. A sterilized cross-linked gelatin composition characterized by a fluid absorbability of at least 30 grams of fluid per gram of gelatin and a tensile strength of greater than 2.0 lbs/in$^2$.

7. The sterilized cross-linked gelatin composition of claim 6 wherein said composition has a fluid absorbability of at least 35 grams of fluid per gram of gelatin and a tensile strength of greater than 2.5 lbs/in$^2$.

8. The sterilized cross-linked gelatin composition of claim 6 wherein said composition further comprises an antimicrobial agent, a growth factor, a thrombus enhancing agents or mixtures thereof.

9. The sterilized cross-linked gelatin composition of claim 8 wherein said antimicrobial agent is an antibiotic.

10. A method for preparing a sterile syringe comprising a cross-linked gelatin composition wherein said syringe is included in a packaging element which method comprises:
    (a) selecting a syringe assembly comprising a holding chamber an injection port which comprising a luer hub and an ejection port which is attached to a cannula;
    (b) adding to the holding chamber of said syringe a cross-linked gelatin composition in the form of a pledget;
    (c) adding sterile saline to said holding chamber wherein sufficient amounts of said saline are added to hydrate said pledget;
    (d) transferring the hydrated pledget into the cannula attached to the ejection port;
    (e) combining at least a single syringe produced in (d) above into a packaging element;
    (f) exposing the packaging element formed in (e) above to a sufficient dosage of E-beam irradiation maintained at an initial fluence of at least 5 μCurie/cm$^2$ to sterilize the packaging element and the syringe and the gelatin composition therein
    wherein the average bulk density of the materials comprising the packaging element is less than about 0.2 gm/cm$^3$ and wherein said cross-linked gelatin composition retains a sufficient amount of fluid absorbability and tensile strength.

* * * * *